United States Patent

Kraus

[11] 3,973,929
[45] Aug. 10, 1976

[54] METHOD AND APPARATUS FOR ENRICHING A LOWER MOLECULAR WEIGHT GAS WITH SUBSTANCES OF HIGHER MOLECULAR WEIGHT CONTAINED THEREIN

[75] Inventor: Thaddäus Kraus, Triesen, Furstentum, Liechtenstein

[73] Assignee: Balzers Patent und Beteiligungs AG, Liechtenstein

[22] Filed: July 5, 1974

[21] Appl. No.: 486,067

[30] Foreign Application Priority Data
July 12, 1973   Switzerland...................... 10209/73

[52] U.S. Cl........................................ 55/17; 55/25; 55/57; 55/472
[51] Int. Cl.²........................................ B01D 45/12
[58] Field of Search ..................... 55/17, 25, 57, 58

[56] References Cited
UNITED STATES PATENTS

| | | | |
|---|---|---|---|
| 2,657,802 | 11/1953 | Reed................................... | 55/17 X |
| 3,546,891 | 12/1970 | Fekete................................ | 55/17 X |
| 3,613,989 | 10/1971 | Oyama et al....................... | 55/17 X |

FOREIGN PATENTS OR APPLICATIONS

| | | | |
|---|---|---|---|
| 2,087,102 | 12/1971 | France................................. | 55/17 |
| 1,247,069 | 9/1971 | United Kingdom.................... | 55/17 |

*Primary Examiner*—John Adee
*Attorney, Agent, or Firm*—McGlew and Tuttle

[57] ABSTRACT

A method and apparatus for enriching a gas of lower molecular weight with substances of higher molecular weight contained therein, comprises using first and second molecular pumps connected together, with the second pump having a conveying direction different from the first pump, and wherein a feed line for the gas terminates in a working chamber of the first molecular pump and its exhaust side includes extraction means for the enriching component. The gas is conducted to the working chamber of the first molecular pump and a portion of the gas is conveyed at the intake side of the molecular pump by means of the second pump. The substances of higher molecular weight are collected and extracted at the exhaust side of the first molecular pump.

10 Claims, 3 Drawing Figures

METHOD AND APPARATUS FOR ENRICHING A LOWER MOLECULAR WEIGHT GAS WITH SUBSTANCES OF HIGHER MOLECULAR WEIGHT CONTAINED THEREIN

FIELD AND BACKGROUND OF THE INVENTION

This invention relates in general to the construction of devices for enriching gases and, in particular, to a new and useful device and method for enriching gas substances of higher molecular weight contained therein by means of molecular pumps.

REFERENCE TO TERMS AND THE KNOWN LITERATURE

In the present specification, the term "enriching" means collecting one component under simultaneous increase of the ratio of its amount with respect to the amount of one or several other separable substances. The substance indicated contained in a gas of higher molecular weight may also be a gas, vapors or also suspended matter (aerosol). The invention is important for environmental analysis, such as e.g., the analytic determination and detection of noxious substances in the air and in emissions.

Molecular pumps are indicated among other things in the following list of references:

1. Becker, W.: Ueber eine neue Molekularpumpe. Advances in Vacuum Science and Technology 1960, Vol. 1, p. 173 Pergamon Press
2. Krueger, Ch. H./Shapiro A. H.: Vacuum Pumping with a Bladed Axial-Flow Turbomachine. 7th National Symposium of Vacuum Technology Transactions, 1960 Pergamon Press
3. Hablanian, M. H.: The Axial Flow Compressor as a High Vacuum Pump. Advances in Vacuum Science and Technology 1960, Vol. 1, p. 168, Pergamon Press
4. R. B. Jacobs: The Design of Molecular Pumps, J. Appl. Physics Vol. 22 (1951) Nr. 2, p. 217

DESCRIPTION OF THE PRIOR ART

In literature reference 1. above, the assumption is expressed that molecular pumps may be employed for the separation of light isotopes. It is referred to the fact that these pumps attain a compression of 250:1 for light hydrogen ($H_2$), while it increases to 2400:1 for heavy hydrogen ($D_2$). By designating as separation factor the number which indicates how many times greater the compression of the more compressed component is, than that of the less compressed component, a separation factor of 9.6 would result for the above case. It is to be expected accordingly that after a sufficient long time of pumping the ratio $D_2/H_2$ in the collecting vessel (at the discharge end) is 6.9 times larger than in the storage tank (at the intake end of the pump).

If, however, one expects, on the basis of the state of the art, an enrichment when the gas mixture to be separated is pumped from a storage tank into a collecting vessel, he will be disappointed. Although the expected pressure ratio for each component of the gas mixture sets in between the intake and the discharge end, it is surprising that the mixing ratio of the components in the collecting vessel (on the discharge side of the pump) hardly differs from the mixing ratio of the original mixture. Indeed, the pressure ratio stated above sets in for each of the components practically exclusively due to the fact that owing to the pumping effect, the partial pressures change in the storage tank (suction side), and the partial pressure of the heavy component diminishes in comparison with the partial pressure of the lighter component by the amount of the separation factor.

This effect may be utilized for the detection of leaks in vacuum plants (literature reference 2): the vacuum chamber to be tested is sprayed on from the outside with a test gas of low molecular weight, for example, hydrogen or helium, and the test gas penetrates through possible leaks into the chamber from which it is aspired by means of a pump together with the other gas existing in the chamber. In order to detect the gas which penetrated, a branch line on which a molecular pump is mounted, leading to a pressure measuring instrument, is connected to the suction line, and the molecular pump acts against the penetration of gases into the pressure measuring instrument. Since the test gas has a smaller molecular weight, it can reach much easier the pressure measuring instrument against the conveying effect of the molecular pump than the remaining heavier gas, for example, air. In this way, the pressure in the pressure measuring instrument increases as soon as the test gas penetrates the vacuum chamber through a leak. However, no enrichment of the test gas takes place herewith. On the contrary, a lower pressure prevails in the pressure measuring instrument, corresponding to the compression of the molecular pump, rather than in the vacuum chamber. Accordingly, a smaller amount of test gas would be available for an analytical detection than if the detection instrument were directly connected through the branch line with the suction line, that is, without intercalation of a molecular pump.

Consequently, an enriching in the above sense appeared as not being possible on the basis of the state of the art. In any event, a separation of only the lighter component can be achieved whereby its partial pressure is greater with respect to the partial pressure of the heavier component, but in its absolute value, becomes smaller than without use of a molecular pump. According to the above definition, not even a separating effect for the heavier component can be ascertained. Compared with this, it is an object of the invention to enrich a gas with a heavier component contained therein, in the sense state above, particularly for improving the analytical detection of heavier components.

An object of the invention is to achieve a uniform enrichment degree for substances of different molecular weights.

A further object of the invention is to achieve a defined enrichment degree in a minimum period of time.

A further object of the invention is to provide a device for enriching a gas of lower molecular weight with a substance of higher molecular weight which includes a first molecular pump connected to a second pump which has a conveying direction different from the first, wherein a feed line is connected into the working chamber of the first molecular pump and the exhaust of the working chamber is provided with means for extracting the enriching component.

For an understanding of the principles of the invention, reference is made to the following description of typical embodiments thereof as illustrated in the accompanying drawings.

DESCRIPTION OF THE PREFERRED EMBODIMENTS

Figure 1:
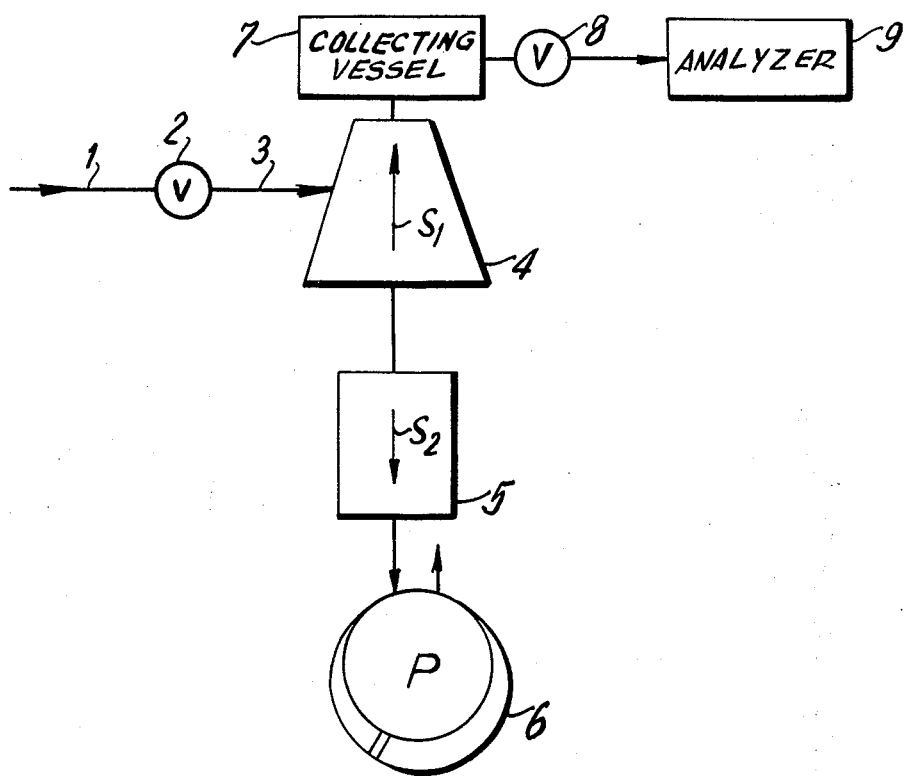
FIG. 1 is a schematic view of an apparatus for mixing a gas of lower molecular weight with substances of higher molecular weight which are contained therein.

Referring to the drawings in particular, the invention embodied therein in FIG. 1, comprises an apparatus or arrangement for enriching a gas of lower molecular weight with substances of higher molecular weight contained therein and which includes a supply line 1 for a gas which contains the component with which it is to be enriched. The gas is fed through a valve 2 and a line 3 to a molecular pump 4. The conveying action of molecular pump 4 has the direction indicated by the arrow $S_1$. A second pump 5, of any type per se, is connection with pump 4 and the conveying direction is also shown in FIG. 1 by an arrow $S_2$ is an opposite direction to that of pump 4. The major portion of the gas fed over 1 to molecular pump 4 is carried away by means of pump 5 and finally by a fore pump 6, while the heavy enriching rest is collected in a collecting vessel 7. From this collecting vessel, the enriching heavy component can be extracted through a valve 8 and fed, for example, to an analyzer 9. The conveying directions of pumps 4 and 5 are opposite to one another, as shown in FIG. 1.

Figure 2:
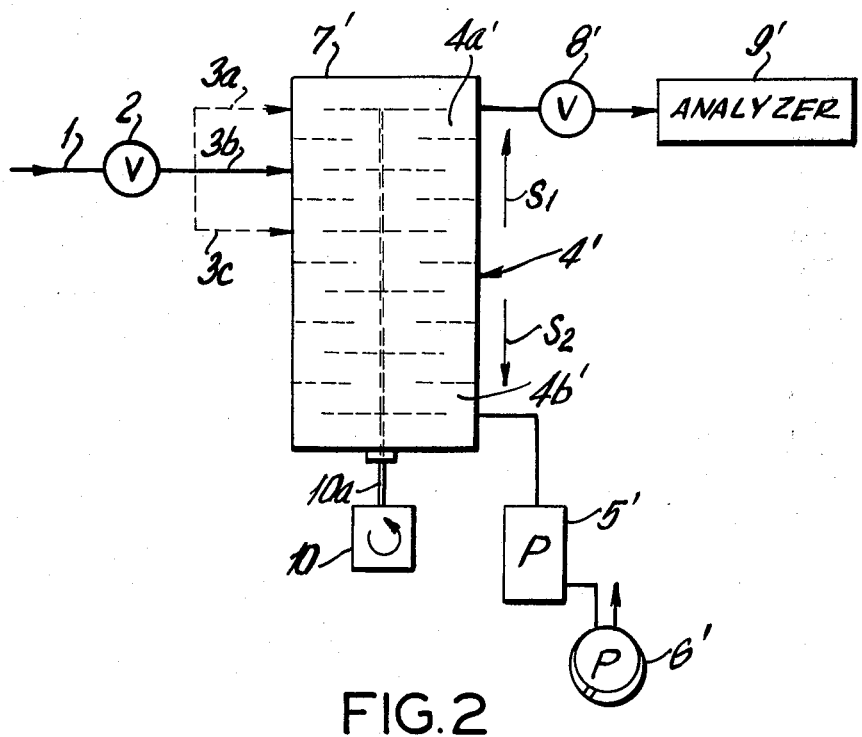
FIG. 2 is similar to FIG. 1, but shows another embodiment of the invention.

The diverging of the two conveying directions must not, however, be applied to an external connecting point of the pumps 4 and 5, but may be carried out particularly advantageously, for example, with two sets of molecular pump stages pumping in opposite directions within the same pump housing, as shown in the embodiment in FIG. 2. A molecular pump 4' has several stages which are divided into two groups acting as one or more first and second partial pumps $4a'$ and $4b'$, with divergent conveying directions, as indicated by arrows $S_1$ and $S_2$. The gas intake occurs within the range of the conveying direction $S_1$ or between both partial pumps. Employable double molecular pumps are described, for example, in reference 13. An enriching in the sense of the invention is attained with three intake points $3a$, $3b$, $3c$, or with other intake points in between. It is only important that the gas feed reaches the action range of at least one of the stages of the molecular pump $S_1$. In the described embodiment, the dead space of the pumps acts as a collecting vessel.

For a better understanding of the following statements, it is suitable to characterize the enrichment with the heavy component by the following term, the "enrichment degree" $\alpha$:

$$\alpha = \frac{n_s}{n_l} \cdot \frac{Q_l}{Q_s} = \frac{n_s}{n_l} \cdot \frac{Q_l \cdot t}{Q_s \cdot t} \approx \frac{c_s''}{c_s'} = \frac{n_s}{n_l} \cdot \frac{1}{c_s'} \quad (1)$$

where $n_s$ is the amount of the heavy component and $n_l$ the amount of the light component in the collecting vessel 7, and $Q_l$, $Q_s$, the amount of light and heavy component, respectively introduced per unit of time into the molecular pump through line 3.

From the form indicated to the right above, in which the fraction was expanded with the time $t$ necessary for collecting the amounts $n_s$ and $n_l$, the following can be seen:

$Q_s.t$ and $Q_l.t$ are the amounts of the heavy and light components, respectively, which were fed in the time $t$ to the separation arrangement. These amounts are not identical with the amounts $n_s$ and $n_l$, because a portion of the amounts supplied by means of pump 5' is again carried away.

Accordingly, $n_s/Q_s.t$ indicates the fraction of the amounts of the heavy component which was actually collected in collecting vessel 7 and correspondingly $n_l/Q_l.t$, the respective fraction for the light component. The foregoing defined enrichment degree $\alpha$ for the heavy component is consequently, as may be seen, equal to the ratio of these two fractions. It indicates to which extent the heavy component is more retained in the collecting vessel than the undesired lighter component. According to this definition of the enrichment degree, it is indifferent if the accumulated amount of substance $n_s$ is present in a gaseous or in a condensed state.

The concentration $c_s'$ of the enriching components in the gas flowing in are generally so small that they may be equated with the ratio of quantities $Q_s.t/Q.t$. When the enrichment degree $\alpha$ is known, this results in the possibility of calculating the concentration in the gas flowing in from the amounts respectively from the concentration in the collecting vessel. If, for example, $\alpha = 1000$, the concentration $c_s'$ in the gas flowing in will be 1000 times smaller than the concentration $c_s''$ in the collected gas. If the accumulated substance is condensed, on the other hand, then only the form indicated to the extreme right may be used for calculating the concentration $c_s'$ in the gas flowing in. Accordingly, the knowledge of the enrichment degree $\alpha$ forms, in any case, a prerequisite for quantitative analyses.

In order to determine the enrichment degree $\alpha$, it is recommended that a gas stream of known concentration be introduced, and that the partial pressure of the respective component in collecting vessel 7 be determined, for example, by means of a mass spectrometer. In particular, vapors whose partial pressures can be precisely set in a well-known manner by the temperature of a sample of the substance and which may be found in vapor pressure tables, such as, for example, mercury, are most suitable for producing a gas stream of known concentration. The gas stream, conducted over the sample of the substance, is introduced into the molecular pump through valve 2. Its amount $Q_l$ must be continuously adjusted, in order that the total pressure in the collecting vessel 7 ensures a molecular flow, and thus, a complete separating action of the molecular pump. This is the case, according to the construction of the pump, at pressures below 0.1 torr. The enrichment degree $\alpha$ is obtained by means of formula (1) from the ratio of the concentrations in the collected gas and in the gas flowing in.

The period of time necessary for attaining a certain enrichment degree $\alpha$ is designated hereinbelow in "enrichment time" $t$. It starts as soon as the inlet valve 2 is opened after evacuating the collecting vessel 7 with closed valve 8. In ample investigations, it was found that, in the arrangement described, the enrichment time $t$ is proportional to the enrichment degree $\alpha$, to the compression $C_l$ of the pump for the light main component, to the effective volume V of the collecting vessel, and is inversely proportional to the effective capacity S of the arrangement. In general, the effective capacity S is somewhat smaller than the nominal capacity of the molecular pump, while the effective volume V of the collecting vessel is somewhat greater than its measurable volume. Considering these deviations, the relationship found can be expressed by the approximation formula:

$$t \approx \alpha \cdot C_l \cdot V/S \qquad (2)$$

Based upon this formula, it appears to be possible to determine the enrichment degree $\alpha$ from the enrichment time $t$. However, since the values S and V, as previously mentioned, cannot be determined with the sufficient accuracy required by the analyses, it is recommended that the value of the quotient $C_l \cdot V/S$ be calculated for the respective light main component from the measured values of $t$ and $\alpha$. By means of this value, the unknown concentrations $c_s'$ in the gas flowing in can be determined from the measured concentrations $c_s''$ in the collected gas, and from the enrichment time $t_l$, which can be varied within large limits according to the concentration range in which the operation has to take place.

By means of a molecular pump, available in commerce (nominal capacity S = 250 liters/sec., compression for air $C_l$ = 50,000 : 1, measured volume of the collecting vessel V = 0.1 liters) by way of example, for heptane (molecular weight about 100) for $\alpha$ = 1000 in air, an enrichment time of $t$ = 10 hours was necessary. Repeating this experiment with mercury (molecular weight about 201) and also with uranium hexafluoride (molecular weight about 352), the same enrichment time was obtained.

Accordingly, under defined conditions (in the case of the example for substances with molecular weights of 100 and over in air), despite large differences of the molecular weights, surprisingly, equal enrichment times can be relied on. In this special case, unknown concentrations $c_s'$ in the gas flowing in can be determined by dividing the concentrations $c_s''$ measured in the collected gas after an enrichment of 10 hours, by a value $\alpha$ = 1000 independent of the substances. This is particularly advantageous when several or unknown components have to be determined. For this reason, conditions under which the enrichment time is independent of the molecular weight of the accumulated components were investigated, and for this purpose, the compression of the lighter components was varied. This is possible in a very simple manner by changing the speed of the pump, but constructional measures, such as, for example, the change of the number of stages, leads to the same result.

It was found that the enrichment time $t$ is independent of the molecular weight of the accumulated component when the compression $C_l$ of the light main component exceeds a definite minimum value $C_{min}$, thus when $$C_l > C_{min} \qquad (3)$$

For example, in the above investigation arrangement, the compression of the pump for air was reduced to about 5000 : 1 by reducing the rotational speed of the pump. As a consequence, the enrichment time for $\alpha$ = 1000 with heptane (molecular weight 100) was indeed shortened to 2 ½ hours, but for mercury (molecular weight 201) and also for uranium hexaflouride (molecular weight 352), the same enrichment degree resulted after $t$=1 ½ hours. Consequently, in the case of the example, the compression was insufficient for attaining the same enrichment times for all of the three substances, but was sufficient for two of the heavier substances only.

It was further found that the enrichment time is of a minimum value when the compression of the light main component has a certain value $C_{min}$, that is, when $$C_l = C_{min} \qquad (4)$$

Thus, when the compression $C_l$ is greater or smaller than the value of $C_{min}$, the enrichment time $t$ will always be greater than its minimum value $t_{min}$.

Figure 3:
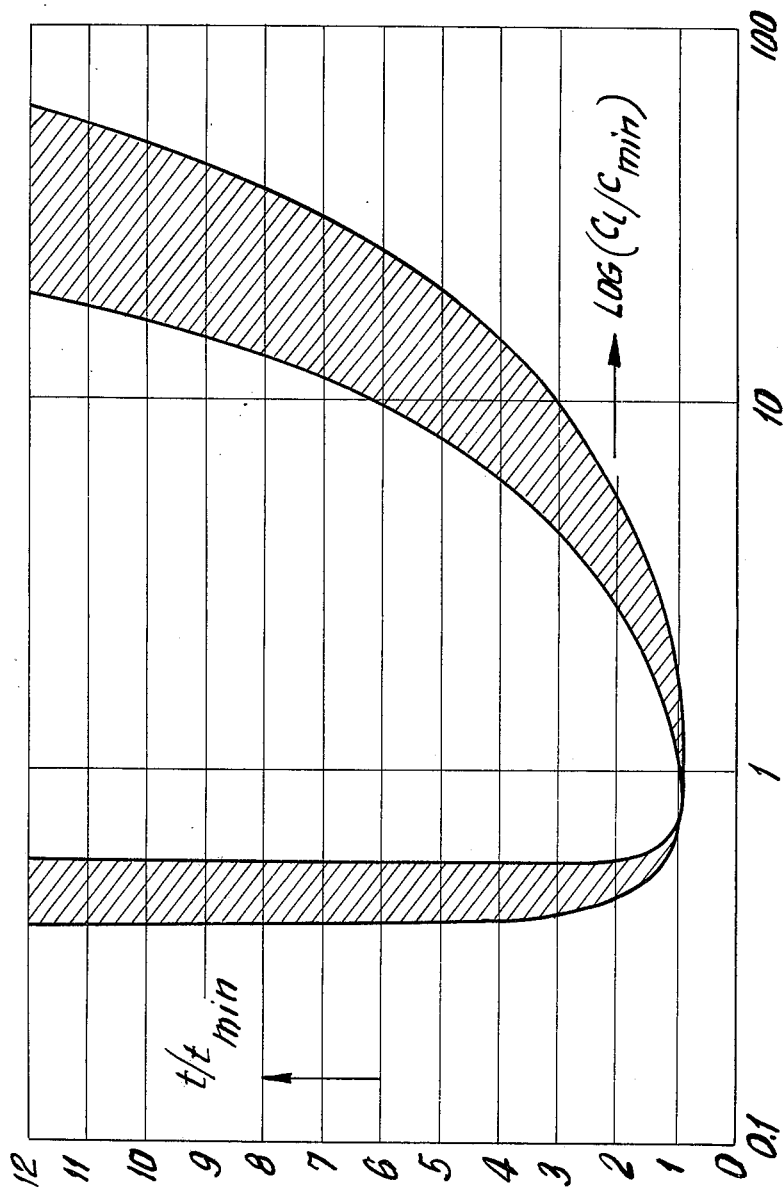
FIG. 3 is an operating curve for the two systems shown in FIGS. 1 and 2.

The diagram in FIG. 3 illustrates the functional relationship between the dimensionless quotient $t/t_{min}$ on linear scale, and the quotient $C_l/C_{min}$, which is also dimensionless, on logarithmic scale. The hatched areas indicate the dispersion range caused by the variable molecular weights. It can be noted from this diagram that, for example, a higher compression by the factor 10 prolongs the enrichment time according to the molecular weight of the enriching component by a factor between 3 and 7. At a still larger deviation, and particularly at compression which is too low, the enrichment time increases considerably, and in the latter case, the approximation formula (2) is no longer valid.

In order to achieve the best possible uniform enrichment times, according to formula (3), and also to achieve the shortest possible enrichment times, according to formula (4), a knowledge of the value of $C_{min}$ is necessary. For this reason, it was investigated to determine upon which factors $C_{min}$ depends. It was found that this value depends upon the enrichment degree $\alpha$, on the molecular weight $M_1$ of the light main component, and upon the molecular weight $M_s$ of the enriching heavy component, whereby, the functional relationship can be expressed in a way of approximation by the formula:

$$C_{min} \approx a \cdot \alpha^{b \cdot M_1/M_s} \qquad (5)$$

In this formula, $b$ is a constant having a value between 3.5 and 4, and another constant approximately equal with $b$. Since this formula comprises only quantities which are known, at least approximately, it can be used for calculating an approximation value for $C_{min}$, regardless of which substances are used to form the gas mixture, only inasmuch as $M_s$ is more than three times greater than $M_1$. Naturally, more accurate values are obtained when the constant $a$ and $b$ are determined experimentally by means of the respective molecular pump on the basis of the functional relationship between enrichment degree $\alpha$ and compression $C_1$, where the enrichment time $t$ amounts to a minimum.

In a particular development of the invention, the molecular pump is operated with such a compression $C_1$, and that for all of the enriching components, it is provided that the enrichment times be equally long and in spite of this, as short as possible. In this case, the necessary compression $C_1$ is calculated according to formulas (4) and (5), where the 0.75-fold value of the lowest molecular weight of the enriching components is employed for $M_s$. On the other hand, if only one component is to be accumulated in the shortest time, the necessary compression $C_l$ is also calculated according to formulas (4) and 5(5), but for $M_s$, the respective component will be used.

It is also suitable to close the valve 2 shortly before extraction of the enriched gas from collecting vessel 7, as shown in FIGS. 1 and 2. This measure cause a very quick decrease of the partial pressure of the light component in the collecting vessel, while the partial pressure of the heavy component remains practically unchanged. By way of example, mercury vapors in air could be detected by means of a certain mass spectrometer without previous enriching down, to a concentration of about 1 ppm by volume, which results in the saturation of air with mercury at +14°C. In this case, with a 1000-fold enrichment, a mercury content of $10^{-3}$ ppm could be determined, which sets in by saturation of air with mercury at minus 46°C.

If shortly before extracting the sample, however, further air supply was stopped, with the same arrangement in about the same time, a mercury content of about $10^{-6}$ ppm could be detected, resulting in the saturation of air with mercury at minus 85°C.

Mercury was chosen for the examples as enriching component because it is very suitable for experimental testing. However, any other desired substance can be chosen as enriching component, providing that its molecular weight is sufficiently high, preferably more than three times the molcular weight of the main component.

The larger the molecular weight $M_s$ of the enriching heavy component is with respect to the molecular weight $M_1$ of the light main component, the smaller the value of $C_{min}$ becomes, according to the formula 5; the smaller the compression $C_1$ to be chosen becomes, according to formula (3) or (4), and finally, the shorter the enrichment time $t$, according to formula (2). Accordingly, by way of example, by means of the above mentioned investigation arrangement, the following minimal times were found for a 1000-fold enrichment: for heptane $t_{min} = 2$ ½ hours, for mercury $t_{min} = 5$ minutes, and for uranium hexafluoride $t_{min} = 1$ ½ minutes. Here, the adjustment of the compression was made by diminishing the rotational speed, which also resulted in a decrease of the pumping capacity S. Consequently, at a constant pumping capacity, the minimum enrichment times would more substantially decrease with increasing molecular weight.

The enrichment times indicated in the examples can still be considerably shortened when molecular pumps with very high pumping capacity S are employed (see formula (2)). The construction of molecular pumps with correspondingly high pumping capacity basically presents no difficulties, particularly if the molecular pumps are destined exclusively for enriching with substances of high molecular weight and, in this connection, no high compression is used.

The known molecular pumps usually provide a higher compression at the rotational speeds at which they are usually operated in the case of pure pumping arrangements than is desirable for the purpose of the invention, according to the aforementioned formulas. It is possible, however, to reduce the rotational speed in order to adjust the compression to the suitable value. Thus, it is practical to provide an arrangement for changing the rotational speed of the molecular pump in an arrangement for carrying out the method in accordance with the invention, in order to make the adjusting to various cases of application possible. Such a driving device, with rotational speed regulation is indicated schematically at 10, in FIG. 2.

In view of the minimal enrichment times which decrease with increasing molecular weights, and the possibilities of improvement as mentioned, it is to be expected that the arrangement described is also applicable to the enrichment with substances of very high molecular weights up to the size of aerosol particles and also when these substances are present in extremely small particle number densities. It thus appears to be possible that in this manner, for example, such noxious substances may also be subjected to enrichment in air and fed to an analytical determination which does not condensate or condensate except with difficulty, and therefore, have up to now eluded enrichment and accurate analytical determination.

A particular advantage of the described enrichment method is that the water vapor contained in air is not eliminated, but is separated in each case, together with the air, because it has a lower molecular weight than air. It is of no importance for the enrichment process if the concentrations of the enriching substances in the inflow are much smaller or much greater than their concentrations in the vaporization equilibrium, i.e., it is of no consequence if there are "overheated" or "supersaturated" vapors. The analytical method has merely to be chosen correspondingly according to the gaseous or condensed state of the substance after enrichment. There are numerous analytical methods available for the microanalytical investigation in connection with the arrangement described. Aside from the mass spectrometry already mentioned, there are also UV, light and IR spectrometry, gas, thin-layer and gel chromatography, nuclear resonance and flame spectroscopy, etc.

In order to obtain a condensable component in the form of a solution, it is useful to apply a small amount of a liquid of high molecular weight in a thin layer at the place of the molecular pump at which the enriching component condenses. Suitable components are, for example, higher hydrocarbons, esters of phosphoric acid, of phtalic acid, of a sulfonic acid, of a higher saturated or unsaturated fatty acid, of multivalent aliphatic acid and also esters of multivalent alcohols (particularly glycerin), higher chlorinated hydrocarbons, polyalkylene glycols, polymers of chlorotrifluoroethylene and some products available in commerce whose chemical structure is uncertain or unknown, such as, plasticizers, lubricants or pump fluids for diffusion pumps.

Particularly appropriate are polymer methyl siloxances which are available in commerce under the designation "silicone oils". This group comprises an enormous range of molecular weights and viscosities and also has liquid phases at the highest molecular weights at which other organic polymers are already solid. Additionally, polymer methyl phenyl siloxanes and other organosiloxanes are proper. When making the choice, attention should be paid to the fact that the saturation vapor pressure of the liquid has to be so small at the operating temperature of the pump, that a molecular flow and therefore a complete separation effect of the pump, be maintained. However, if the liquid evaporates in noticeable amounts, the condensate deposited in the collecting vessel can again be conducted back into a zone of lower pressure where it evaporates again. In the simplest embodiment, this takes place by the vertical arrangement of the shaft 10a, as represented in FIG. 2. The enrichment then occurs on the surface on which the condensate evaporates again. The extraction achieved after enrichment can be carried out by opening and rinsing out by means of a volatile solvent.

While specific embodiments of the invention have been shown and described in detail to illustrate the application of the principles of the invention, it will be understood that the invention may be embodied otherwise without departing from such principles.

What is claimed is:

1. A method for enriching a gas of lower molecular weight with substances of higher molecular weight contained therein using a first molecular pump and a second pump each having a working chamber, comprising conducting the gas to the working chamber of the first molecular pump and conveying away a portion of the gas at the intake side of the first molecular pump directly to the second pump, operating the second pump with gas taken directly into its inlet from said first pump to convey the substances in an opposite direction, and collecting the substances of higher molecular weight at the exhaust side of the first molecular pump for a certain time until they are concentrated and then extracting the concentrated substances of higher molecular weight.

2. A method according to claim 1, wherein said first pump is employed having for the gas of lower molecular weight a compression $$C_1 \approx a \cdot \alpha^{b \cdot M_1 / M_s}$$

where $a$ is a constant having a value between 3 and 10, $b$ is a constant having a value between 3.5 and 4, $\alpha$ the enrichment degree, $M_1$ the average molecular weight of the gas to be separated of lower molecular weight, and $M_s$ the molecular weight of the enriching substance.

3. A method according to claim 1, wherein said first pump is employed for the enrichment with several components, having for the gas of lower molecular weight, a compression $$C_1 \approx a \cdot \alpha^{b \cdot M_1 / M_s}$$

where $a$ is a constant having a value between 3 and 10, $b$ a constant having a value between 4.5 and 5.5, $\alpha$ the enrichment degree, $M_1$ the molecular weight of the gas of lower molecular weight, and $M_s$ the molecular weight of the lightest of the enriching components.

4. A method according to claim 1, wherein the feeding of the mixture to the molecular pump is interrupted prior to extraction of the enriching component or components.

5. An apparatus for enriching a gas of lower molecular weight with substances of higher molecular weight, comprising a first molecular pump having a working chamber discharging to an exhaust and having an inlet, a second pump operable to convey in a direction opposite to the first pump and having an inlet connected to the inlet of said first pump, a feed line for the gas connected directly to said working chamber of said first pump, and extraction means on the exhaust side of said first pump for extracting the enriching component.

6. An apparatus according to claim 5, wherein said first pump comprises multistage molecular pump, said feed line being connected to an intermediate stage.

7. An apparatus according to claim 5, wherein said feed line is connected to the exhaust side of said first molecular pump.

8. An apparatus according to claim 5, wherein said feed line terminates in the collecting chamber.

9. An apparatus according to claim 5, wherein said second pump is also a molecular pump.

10. An apparatus according to claim 5, including means for changing the rotational speed of said molecular pump.

* * * * *